United States Patent [19]

Obata

[11] Patent Number: 5,222,203
[45] Date of Patent: Jun. 22, 1993

[54] METHOD AND APPARATUS FOR DISPLAYING TRANSLUCENT SURFACE

[75] Inventor: Koei Obata, Kusatsu, Japan

[73] Assignee: Daikin Industries, Ltd., Japan

[21] Appl. No.: 879,460

[22] Filed: May 4, 1992

Related U.S. Application Data

[63] Continuation of Ser. No. 467,545, Jan. 19, 1990, abandoned.

[30] Foreign Application Priority Data

Jan. 20, 1989 [JP] Japan .................................. 1-12158

[51] Int. Cl.$^5$ .................................... G06F 15/72
[52] U.S. Cl. ..................................... 395/126
[58] Field of Search ................ 395/126, 131, 132; 340/703, 729; 364/522

[56] References Cited

U.S. PATENT DOCUMENTS

| | | | |
|---|---|---|---|
| 4,475,104 | 10/1984 | Shen | 340/729 |
| 4,709,231 | 11/1987 | Sakaibara et al. | 364/522 X |
| 4,866,637 | 9/1989 | Gonzalez-Lopez et al. | 364/518 |
| 4,897,806 | 1/1990 | Cook et al. | 364/522 |
| 4,901,064 | 2/1990 | Deering | 364/522 X |
| 4,928,250 | 5/1990 | Greenberg et al. | 364/518 |
| 4,943,938 | 7/1990 | Aoshima et al. | 364/522 |
| 4,970,636 | 11/1990 | Snodgrass et al. | 364/518 |
| 5,025,400 | 6/1991 | Cook et al. | 395/126 X |

FOREIGN PATENT DOCUMENTS 137233 4/1985 European Pat. Off. .

OTHER PUBLICATIONS

Whitted, "An Improved Illumination Model For Shaded Display", Communications of the ACM, Jun. 1980, vol. 23, No. 6.

*Primary Examiner*—Mark K. Zimmerman
*Attorney, Agent, or Firm*—Beveridge, DeGrandi, Weilacher

[57] ABSTRACT

A method for displaying a translucent object on a display screen includes a step of displaying a translucent object by providing a diffused transmitted light component instead of a diffused reflection light component and a specular reflection light component as are necessary for displaying an object as an opaque object. A method for displaying a translucent object on a screen also includes a step of judging whether or not an object to be displayed is to be displayed as a translucent object based upon a relation of a viewpoint and a light source to the object to be displayed.

6 Claims, 9 Drawing Sheets

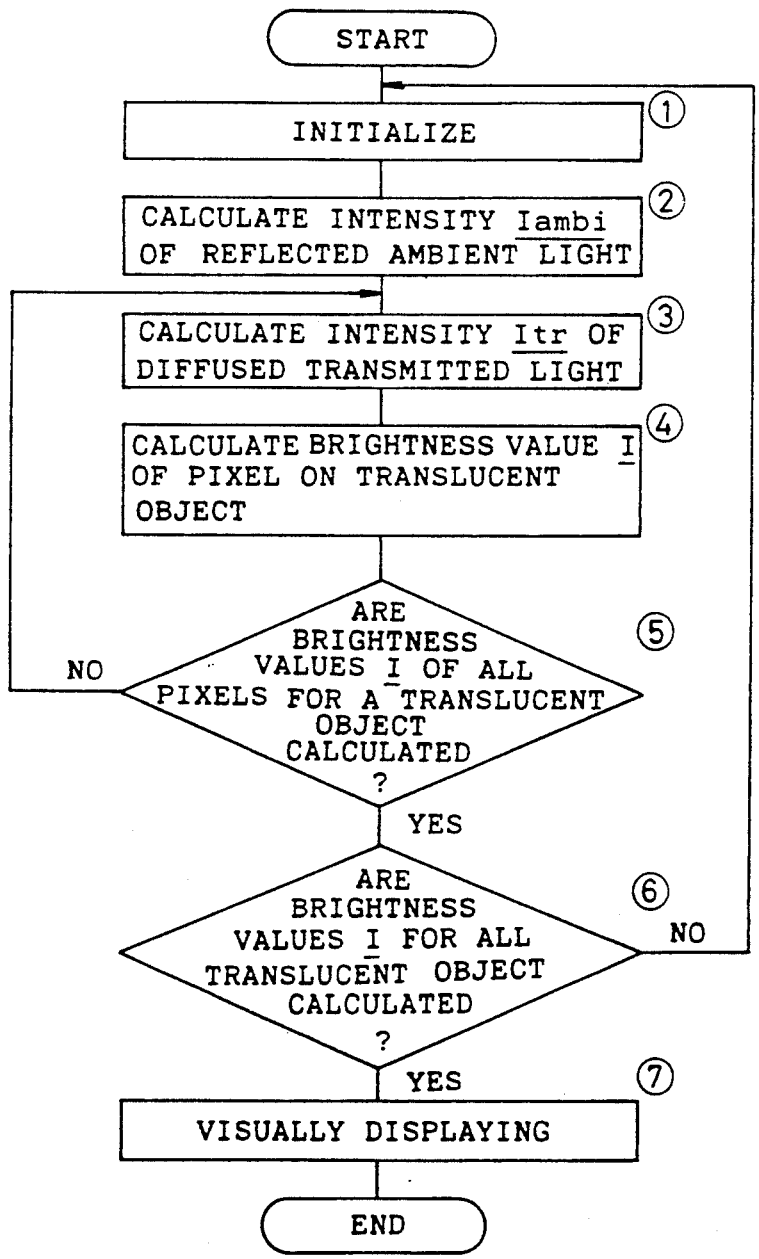

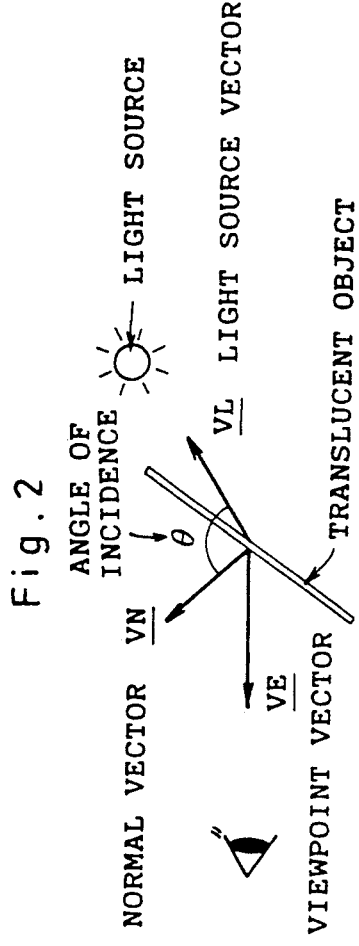
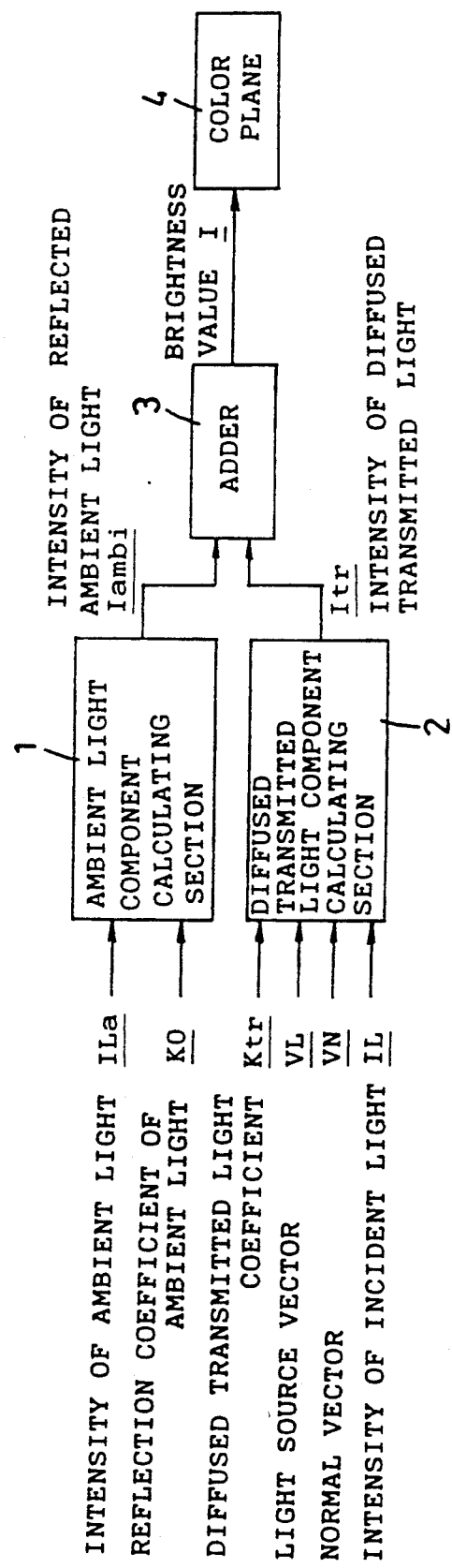

METHOD AND APPARATUS FOR DISPLAYING TRANSLUCENT SURFACE

This application is a continuation, of application Ser. No. 07/467,545, filed Apr. 19, 1990, now abandoned.

BACKGROUND OF THE INVENTION

1. Field of the Invention

The present invention relates to a method and an apparatus for displaying a translucent object, and more particularly, to a method and an apparatus suitable for realistic displaying an object which is not perfectly opaque and which has a fairly low transparency such as frosted glass, paper and the like, by a graphics display apparatus.

2. Description of Related Art

In conventional graphics systems for displaying images of objects, improvements in function are directed to the realistic display of various objects. A display with superior quantitative and qualitative affects can be obtained by selecting whether to display an object surface as an opaque surface or as a translucent surface, corresponding to the type of object.

To be more specific, when a translucent object is displayed in a surface model representation, the object is first defined as a translucent object, then the actual display color is determined by mixing the color of the object and the color of background, based upon the transmissivity of the translucent object. Consequently, when a light source is seen through a translucent object, the light source is displayed with decreased intensity corresponding to the transmissivity of the translucent object, and in color corresponding to the color of the translucent object.

When displaying a translucent object as above-mentioned, a translucent object having high transparency such as cellophane or the like can be displayed realistically. However, a translucent object having a low transparency such as frosted glass or the like is displayed rather different from its actual appearance. That is, the representation of a translucent object having a low transmissivity can be performed by decreasing the mixing rate of light from the light source, but the representation of a translucent surface having a low transparency cannot be performed realistically because the outline of the light source is distinctly displayed as in the case of cellophane or the like. To overcome the disadvantage, modelling of a blurred background such as seen through the translucent object having a low transparency is needed. However, the modelling is not actually performed, and only imperfect displaying of the translucent object is accordingly performed.

When an object to be displayed is paper for example, the object to be displayed is generally defined as an opaque object. However, paper selectively becomes an opaque object or a translucent object, depending upon the relative position of the paper with respect to a viewpoint and a light source. The paper is displayed fairly differently from its actual appearance accordingly. In particular, when a model such as a paper cup is displayed, an opaque portion and a translucent portion are seen, and both portions vary depending upon the relative position of the paper cup to the viewpoint and the light source. A realistic visual display hardly can be obtained accordingly.

SUMMARY OF THE INVENTION

It is an object of the present invention to obtain a visual display with superior realistic appearance for a translucent object having a low transparency.

It is another object of the present invention to obtain a visual display with superior realistic appearance for an object which selectively can become an opaque object or a translucent object depending upon the position of the object.

In order to achieve the above as well other objects, the present invention provides a method for displaying a translucent object on a display screen, which method comprises the steps of:

providing a reflected ambient light component;

providing a diffused transmitted light component based upon light from a light source which light is diffused within a translucent object to be displayed and which light passes through said translucent object;

adding the reflected ambient light component and the diffused transmitted light component to calculate brightness values for the translucent object; and visually displaying the translucent object based upon the calculated brightness values.

The diffused transmitted light component may be calculated based upon a coefficient which is a function of the characteristics of the material forming the translucent object, the thickness of the translucent object, the intensity of incident light from the light source and the angle of incidence of the incident light for illuminating the translucent object. The characteristics of the material include its transmissivity and its transparency.

Also, the diffusing operation includes the reflection of incident light and the refraction of incident light within the translucent object.

In order to achive the above as well other objects, the present invention provides an apparatus for displaying a translucent object on a display screen, the apparatus comprising:

an ambient light component calculating means for calculating a reflected ambient light component;

a diffused transmitted light component calculating means for calculating a diffused transmitted light component based upon light incident on the translucent object from a light source, characteristics of the material forming the translucent object, and the thickness of the translucent object, the diffused transmitted light component being defined as the component of light from the light source which light is diffused within a translucent object to be displayed and which light passes through said translucent object;

brightness value calculating means for calculating brightness values based upon the reflected ambient light component calculated by the ambient light component calculating means and the diffused transmitted light component calculated by the diffused transmitted light component calculating means; and display means for visually displaying the translucent object based upon the brightness values calculated by the brightness value calculating means.

According to the inventive method for displaying a translucent object on a display screen, including the above-mentioned steps, and the apparatus for displaying a translucent object on a display screen, having the above-mentioned arrangement, the reflected ambient light component is obtained by calculation or other methods, then brightness values are calculated based upon the reflected ambient light component and the diffused transmitted light component which arises from light that is passed through the translucent object according to diffusing operations. Thereafter, the translucent object is visually displayed based upon the brightness values thus calculated so as to-blur the outlines of background objects which are seen through the low transparency translucent object. A visual display with superior realism for the translucent object is accordingly obtained.

To be more specific, the inventor discovered that the brightness of a translucent object could be modelled as brightness values determined by the reflected ambient light component and the diffused transmitted light component which arises from light that is passed through the translucent object by reflection and refraction of the incident light. Diffused transmitted light is illustrated together with diffused reflected light in FIG. 10. The present invention was made based upon this discovery. The inventor also discovered that the diffused transmitted light component was determined by the intensity of incident light, the angle of incidence of the incident light and the color of the translucent object, and that the diffused transmitted light component could be calculated fairly accurately by introducing a transmission coefficient for a translucent object instead of a reflection coefficient. Realistic display of the translucent object can be obtained by taking the calculated diffused transmitted light component into consideration.

In order to achieve the above as well other objects, the present invention also provides a method for displaying a translucent object on a display screen, which method comprises the steps of:

judging whether to display an object as a translucent object based upon the relation of a viewpoint vector (a vector starting from a reflecting point and directed to a viewpoint) and a light source vector (a vector starting from a reflecting point and directed to a light source) with respect to the object; and if a judgement is made to display the object as a translucent object, providing a reflected ambient light component, providing a diffused transmitted light component based upon light from a light source which light is diffused within an object to be displayed and which light passes through the object, adding the reflected ambient light component and the diffused transmitted light component to calculate brightness values for the object; and visually displaying the object as a translucent object based upon the calculated brightness values.

The diffused transmitted light component may be calculated based upon a coefficient which is a function of the characteristics of the material forming the translucent object, the thickness of the translucent object, the intensity of incident light from the light source and the angle of incidence of the incident light for illuminating the translucent object. The characteristics of the material include its transmissivity and its transparency.

Also, the diffusion operation includes the reflection of incident light and the refraction of incident light within the translucent object.

In order to achive the above as well other objects, the present invention also provides an apparatus for selectively displaying a translucent object on a display screen, the apparatus comprising:

an ambient light component calculating means for calculating a reflected ambient light component;

judging means for judging whether to display an object to be displayed as a translucent object depending upon the relation of a viewpoint vector, a light source vector and a normal vector with respect to the object;

a diffused transmitted light component calculating means for calculating a diffused transmitted light component based upon light incident on the object from a light source, characteristics of a material forming the object, and the thickness of the object, the diffused transmitted light component being defined as the light component from the light source which light is diffused within an object to be displayed and which light passes through the object;

brightness value calculating means, responsive to a judgement by the judging means that the object should be displayed as a translucent object, for calculating brightness values based upon the reflected ambient light component calculated by the ambient light component calculating means and the diffused transmitted light component calculated by the diffused transmitted light component calculating means; and display means for visually displaying the object as a translucent object based upon the brightness values calculated by the brightness value calculating means.

According to the inventive method for displaying a translucent object, including the above-mentioned steps, and the apparatus having the above-mentioned arrangement for displaying a translucent object, judgement can be made as to whether or not the object should be displayed as a translucent object depending upon the position of the object with respect to the viewpoint vector and the light source vector. When it is judged that the object should be displayed as a translucent object, display of the translucent object as above-mentioned displaying is performed. On the contrary, when it is judged that the object should not be displayed as a translucent object, display of the object as having an opaque surface according to the conventional display method, is performed.

To be more specific, when paper is to be visually displayed, it is generally sufficient that the paper is displayed as an opaque surface. However, it is necessary for realistic display that the paper be displayed as a translucent object depending upon relative positions of a viewpoint and a light source with respect to the paper. The inventor provided a judgement step concerning the relative positions of the viewpoint and the light source to determine whether the viewpoint and the light source are present on the same side of the paper or whether the viewpoint and the light source are on opposite sides of the paper. When the judgement result indicates the former, the paper should be displayed as an opaque object. On the contrary, when the judgement result indicates the latter, the paper should be displayed as a translucent object. Realistic display of the paper is accordingly obtained. The inventor also discovered that the judgement could easily be performed depending upon a result which is obtained by calculations involving the viewpoint vector, the light source vector and the normal vector. Judgement providing the relative positions of the viewpoint and the light source is easily performed accordingly. Consequently, the complexity of operations for visual display can be reduced remarkably.

The above, and other objects, features and advantages of this invention will be apparent from the following detailed description of illustrative embodiments which are to be read with the accompanying drawings.

BRIEF DESCRIPTION OF THE DRAWINGS

FIG. 1 is a flowchart illustrating a first embodiment of a method for displaying a translucent object in accordance with the present invention;

FIG. 2 is a schematic diagram useful in understanding the relative positions of a viewpoint and a light source with respect to a translucent object;

FIG. 3 is a block diagram of an embodiment of an apparatus for displaying a translucent object in accordance with the present invention;

DETAILED DESCRIPTION OF THE PREFERRED EMBODIMENTS

Figure 4:
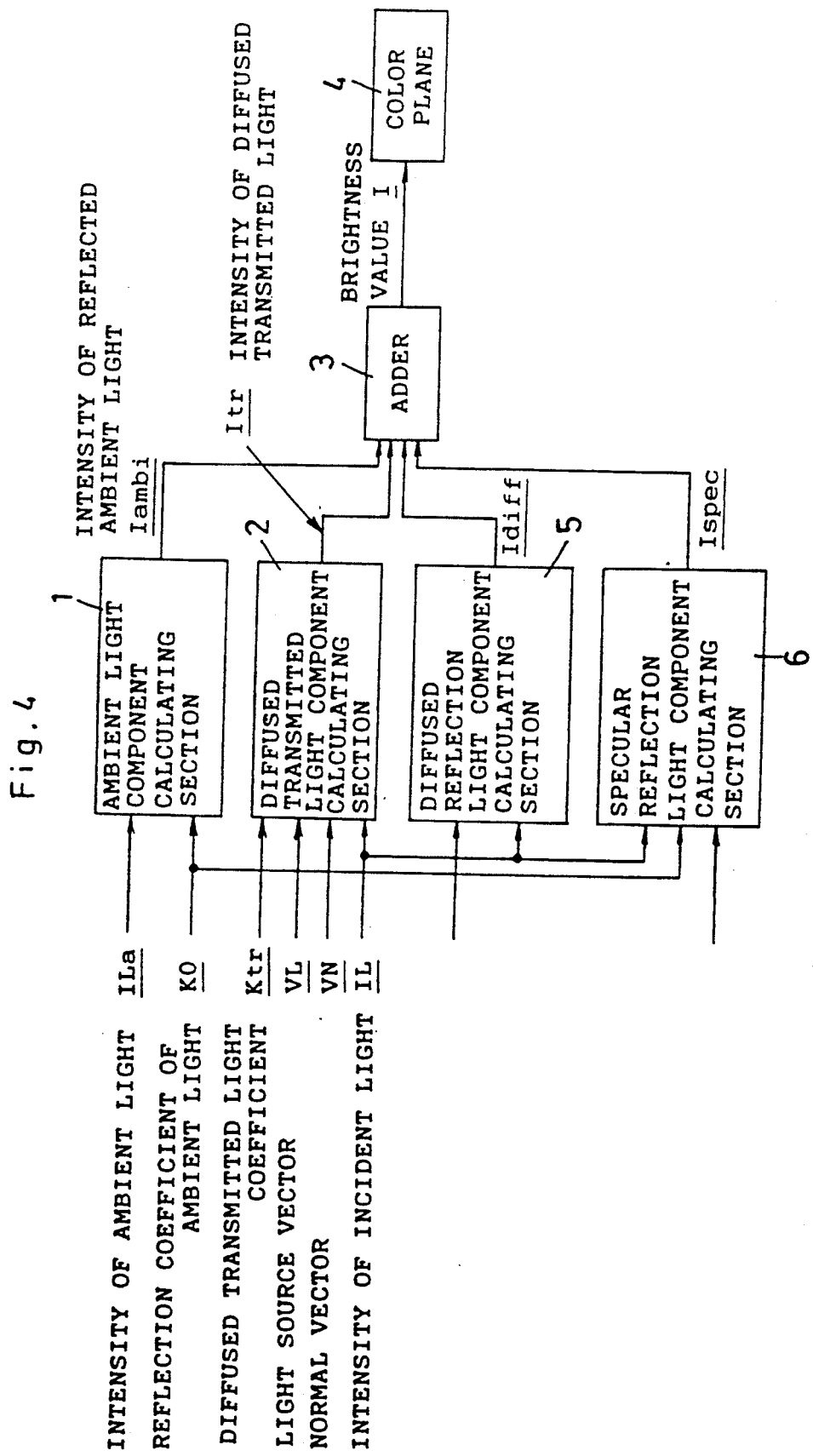
FIG. 4 is a block diagram of another embodiment of the apparatus for displaying a translucent object in accordance with the present invention.

FIG. 1 is a flowchart illustrating a method for displaying a translucent object in accordance with the present invention.

When it is indicated that the display of a translucent object is to be performed, in step (1), the intensity IL of incident light from a light source, a diffused transmitted light coefficient Ktr (coefficient of transmitted light to incident light) for a translucent object, a light source vector VL (refer to FIG. 2), a normal vector VN (refer to FIG. 2) normal to the translucent object and other parameters are initialized; in step (2), the intensity Iambi of reflected ambient light is calculated in a conventional manner; in step (3), the intensity Itr of diffused transmitted light is also calculated. Then in step (4), a brightness value for the translucent object is obtained by adding the intensity Iambi of reflected ambient light and the intensity Itr of diffused transmitted light. Thereafter, in step (5), it is judged whether or not brightness values of all pixels are obtained for a display surface of the translucent object to be displayed. When it is judged that the brightness values of some pixels have not yet been obtained, then processing in step (3) is carried out again. On the contrary, when it is judged that the brightness values of all pixels already have been obtained, then in step (6), it is judged whether or not the brightness values for all translucent objects have been obtained. When it is judged that the brightness values for some translucent objects have not yet been obtained, then processing in step (1) is carried out again. On the contrary, when it is judged that the brightness values for all translucent objects already have been obtained, then in step (7), translucent objects are visually displayed.

In step (3), the intensity Itr of the diffused transmitted light is calculated according to the equation $$Itr = Ktr * IL * \cos \theta$$

(where $\cos \theta = VL * VN$, and * indicates multiplication). Then the intensity Itr which depends upon the angle of incidence of the incident light is obtained. The color of the light source is not taken into consideration in the equation, it is sufficient that calculations also taking color data into consideration are performed when the light source is not white light.

When a translucent object, such as frosted glass, is displayed according to the above-mentioned method, the outline of a light source which is seen through the translucent object is blurred to obtain a superior realistic display of the translucent object. Not only when light from the light source is incident on the translucent object, but when light from the light source is reflected by a background object and is then incident on the translucent object, the outline of the background object is displayed as blurred to obtain a superior realistic display.

FIG. 3 is a block diagram of an apparatus for displaying a translucent object in accordance with the present invention.

The apparatus includes an ambient light component calculating section 1, a diffused transmitted light component calculating section 2, an adder 3 and a color plane 4. The ambient light component calculating section 1 is well known to the person having ordinary skill in the art.

The ambient light component calculating section 1 receives an ambient light intensity value ILa and a reflection coefficient KO, and calculates the intensity Iambi of the reflected ambient light based upon the intensity ILa and the reflection coefficient KO. The diffused transmitted light component calculating section 2 receives the intensity value IL corresponding to incident light from a light source, a diffused transmitted light coefficient Ktr, a light source vector VL and a normal vector VN, and calculates the intensity Itr of diffused transmitted light according to the equation $$Itr = Ktr * IL * \cos \theta$$

(where $\cos \theta = VL * VN$). The diffused transmitted light component calculating section 2 may calculate the intensity Itr also by taking color data into consideration. The adder 3 adds the intensity Iambi of the reflected ambient light and the intensity Itr of the diffused transmitted light to obtain a sum and writes the sum to the color plane 4.

In this embodiment, a brightness value I (=Iambi+Itr) for displaying a translucent object can be obtained by adding the intensity Iambi of reflected ambient light and the intensity Itr of diffused transmitted light which varies depending upon the angle of incidence of the light from the light source.

When a translucent object, such as frosted glass, is displayed by the above-mentioned apparatus, the outline of a light source which is seen through the translucent object is blurred to obtain a superior realistic display of the translucent object. Not only when light from the light source is incident on the translucent object, but when light from the light source is reflected by a background object and is then incident on the translucent object, the outline of the background object is displayed as blurred to obtain a superior realistic display.

FIG. 4 is a block diagram of another embodiment of the apparatus for displaying a translucent object in accordance with the present invention.

The embodiment of FIG. 4 differs from the embodiment of FIG. 3 in that a diffused reflection light component calculating section 5 and a specular reflection light component calculating section 6 are further provided. The diffused reflection light component calculating section 5 and the specular reflection light component calculating section 6 are employed in conventional apparatus for displaying images with shading.

In this embodiment, display of an opaque object can be performed by providing a zero, "0", value output from the diffused transmitted light component calculating section 2. On the contrary, display of a translucent object can be performed by providing "0" value outputs from the diffused reflection light component calculating section 5 and the specular reflection light component calculating section 6. The selection of the above-mentioned states can be performed by setting the coefficient to "0" value, the coefficient being supplied to the corresponding calculating section whose output should be set to "0" value. Consequently, the display of opaque objects and translucant objects can be performed without significantly complicating the arrangement.

Figure 5:
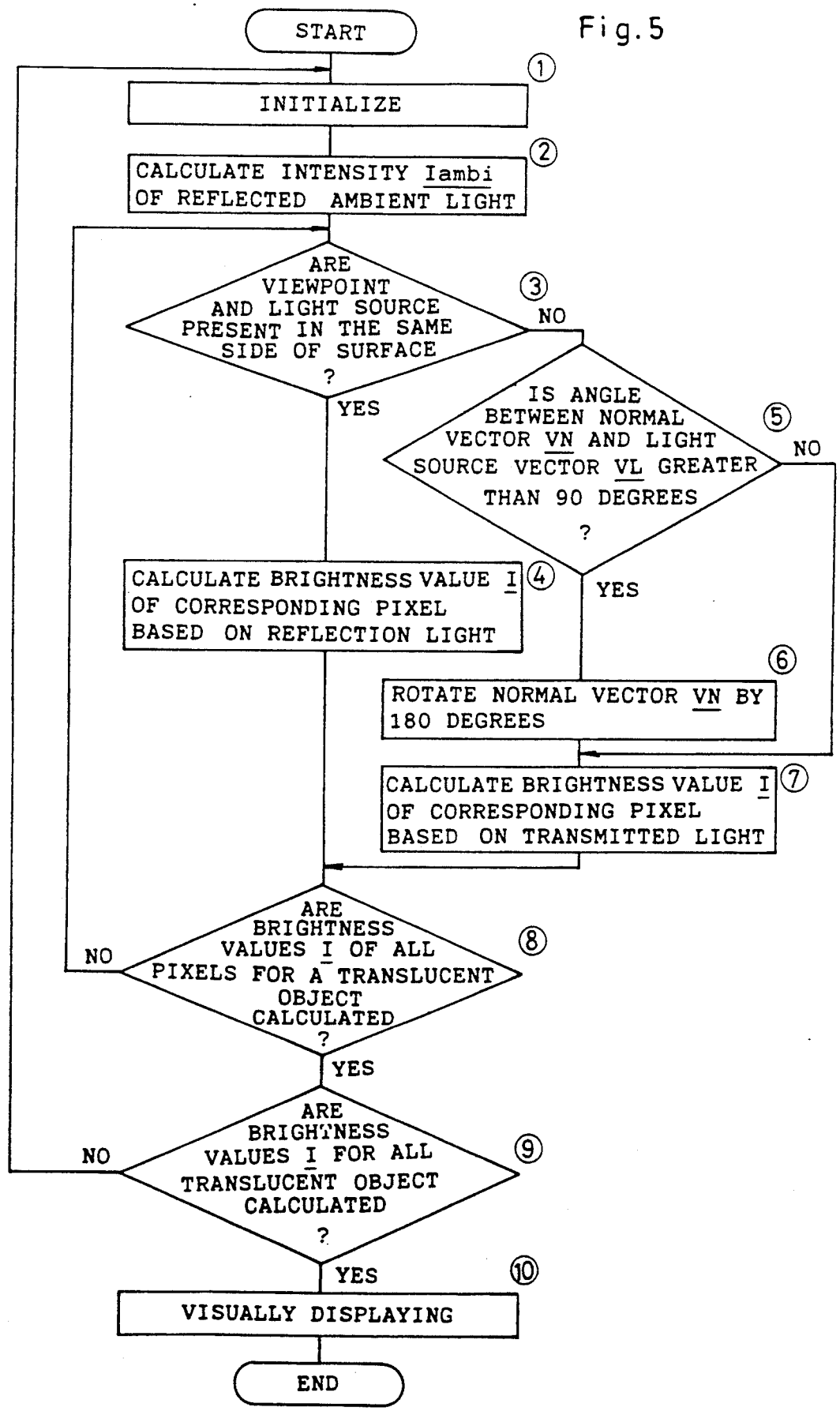
FIG. 5 is a flow chart illustrating an alternative method for displaying a translucent object in accordance with the present invention.

FIG. 5 is a flow chart illustrating an alternative method for displaying translucent objects in accordance with the present invention.

The method illustrated in FIG. 5 differs from the method of FIG. 1 in that a judgement is performed to determine whether or not an object should be displayed as a translucent object.

In step (1), the intensity IL if incident light from a light source, a diffused transmitted light coefficient Ktr, a light source vector VL, a normal vector VN normal to the surface of the translucent object, a viewpoint vector VE and other parameters are initialized; in step (2), the intensity Iambi of reflected ambient light is calculated in the conventional manner. Then in step (3), it is judged whether or not a viewpoint and a light source are on the same side of a display surface of a translucent object to be displayed. The surface is hereinafter referred to as a translucent surface. The judgement is performed wherein, for example, an inner product of the viewpoint vector VE and the normal vector VN and an inner product of the light source vector VL and the normal vector VN are obtained; then it is judged whether or not the product of the inner products is positive. When the viewpoint and the light source are determined to be on the same side of the translucent surface (when the product of the inner products is greater than 0), in step (4), the intensity Idiff of diffused reflection light and the intensity Ispec of specular reflection light are calculated, and then a brightness value I for the corresponding pixel is obtained by adding the intensity values Idiff and Ispec to the intensity value Iambi of the reflected ambient light. On the contrary, when the viewpoint and the light source are determined to be on the opposite sides of the translucent surface (when the product of the inner products is negative), in step (5), it is judged whether or not an angle between the normal vector VN and the light source vector VL is greater than 90 degrees. The judgement is performed by judging whether or not the inner product of the light source vector VL and the normal vector VN, is negative or not. Only when it is judged that the angle is greater than 90 degrees, in step (6), the normal vector VN is rotated by 180 degrees to obtain a normal vector for calculation. Then, in step (7), the intensity Itr of diffused transmitted light is calculated, and a brightness value I of a corresponding pixel is obtained by adding the intensity Itr and the intensity Iambi of the reflected ambient light. After the operation in step (4) or in step (7) is performed, in step (8), it is judged whether or not brightness values for all pixels of the translucent object have been obtained. When it is judged that brightness values of some pixels have not yet been obtained, the operation in step (3) is carried out again. On the contrary, when it is judged that the brightness values of all pixels already have been obtained, then in step (9), it is judged whether or not brightness values for all objects have been obtained. When it is judged that brightness values for some objects have not yet been obtained, the operation in step (1) is carried out again. On the contrary, when it is judged that the brightness values for all objects already have been obtained, then in step (10), all objects are visually displayed.

As is apparent from the foregoing, where multiple objects may require display as a translucent object or display as an opaque object, displaying one or more objects as a translucent object is automatically selected depending upon the relative position of the display surface of the object to be displayed, with respect to the viewpoint and the light source. As a result, a superior realistic display of each translucent object is performed.

Figure 6:
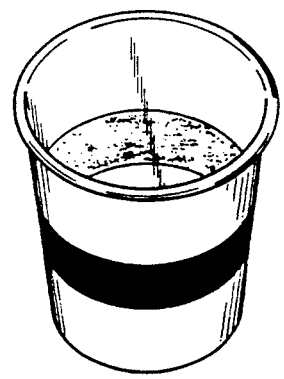
FIG. 6 is a perspective view of a paper cup with a band which requires display of an opaque object and display of a translucent object.

With reference to FIG. 6, when a paper cup which has a red-colored band on its outer surface is to be visually displayed, a portion of the paper cup nearest a light source would have the band on a surface opposite the viewpoint side. The portion nearest the light source would undergo processing for display of a translucent object by using light transmitted through the band as a new light source for display of the nearest-to-the-light-source portion to show the color of the band as blurred when viewed through the inner surface of the paper cup. As to the portion of the cup nearest the viewpoint, this portion is displayed to show the color of the band clearly, without showing the light source at all because of the low transmissivity of the paper. As a result, the paper cup is displayed as fairly similar to its actual appearance.

When a similar display is to be obtained by using conventional method, the band is mapped on the nearest-the-viewpoint surface in a portion through which the band is to be seen by a texture mapping method. The color of the band to be mapped is determined to be faint, corresponding to how the band would be seen through the paper. This results in a remarkably long time period for processing a display and the display is not very realistic.

On the contrary, when a method for displaying translucent objects in accordance with the present invention is employed, the necessary time period for displaying is barely increased and a superior realistic display is provided.

According to the method of FIG. 5, the normal vector VN is rotated by 180 degrees in step (6). However, it is possible to obtain the absolute value of the inner product of the light source vector VL and the normal vector VN. In this case, it is not necessary to judge whether or not the angle between the light source vector VL and the normal vector VN is greater than 90 degrees.

Figure 7:
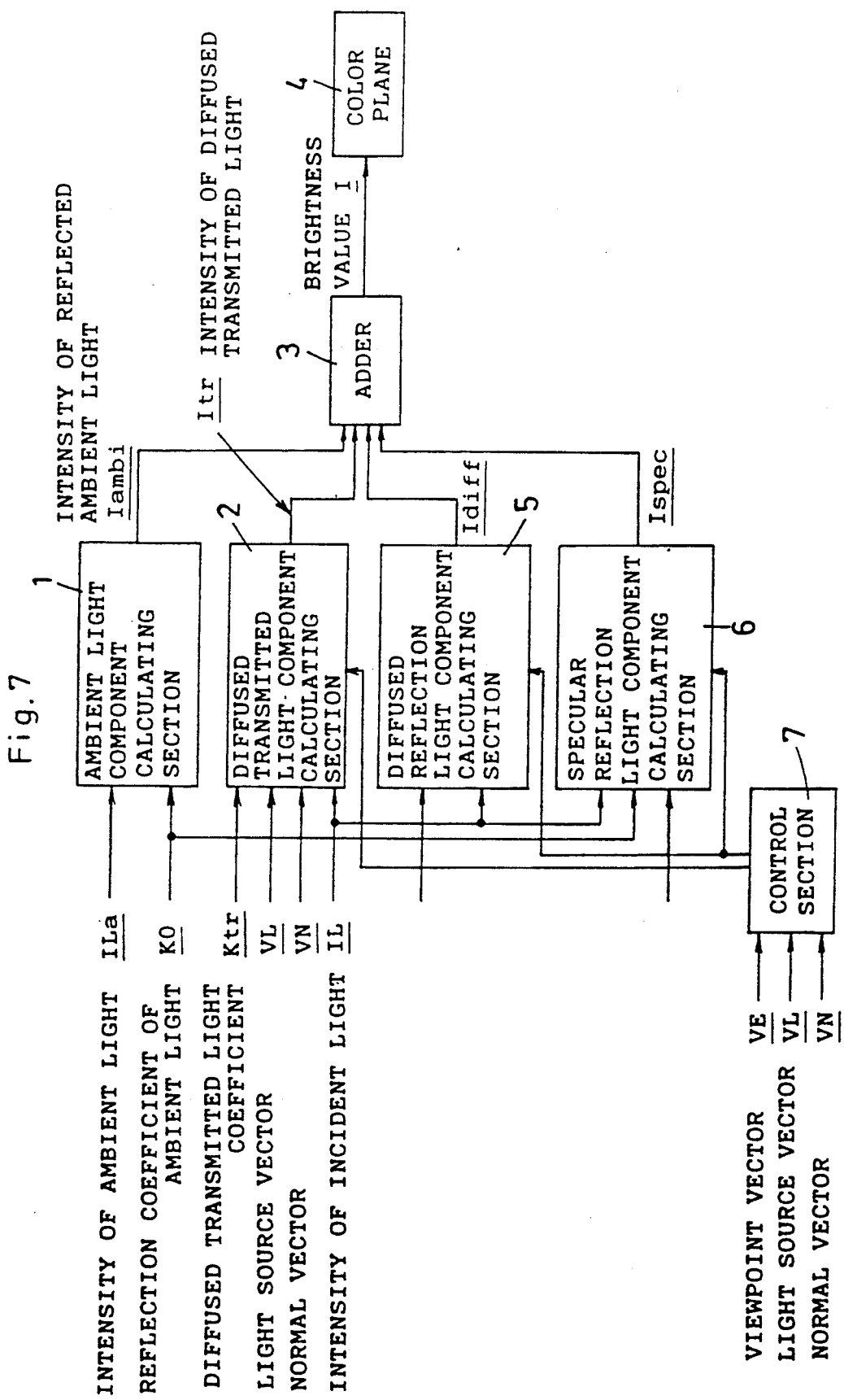
FIG. 7 is a block diagram of still another embodiment of the apparatus for displaying a translucent object in accordance with the present invention.

FIG. 7 is a block diagram of another embodiment of the apparatus for displaying translucent objects in accordance with the present invention.

The embodiment of FIG. 7 differs from the embodiment of FIG. 4 in that a control section 7 is provided for judging whether or not an object should be displayed as a translucent object and for controlling the operation of the calculating sections 2, 5 and 6. The control section 7 obtains an inner product of the viewpoint vector VE and the normal vector VN and an inner product of the light source vector VL and the normal vector VN; then obtains the product of the inner products and, thereafter, outputs a control signal indicative of whether or not the product is negative. The control signal operates only the diffused transmitted light component calculating section 2 when the product is negative, and operates the diffused reflection light component calculating section 5 and the specular reflection light component calculating section 6 when the product is equal or greater than 0. The ambient light component calculating section 1 operates in both cases.

In this embodiment, the control section 7 outputs a control signal depending upon the relative positions of the viewpoint, the light source and the object surface to be displayed so as to automatically select between displaying the object as a translucent object by operating the ambient light component calculating section 1 and the diffused transmitted light component calculating section 2, or displaying the object as an opaque object by operating the ambient light component calculating section 1, the diffused reflection light component calculating section 5 and the specular reflection light component calculating section 6. As a result, there is no need for an operator to designate an object as an opaque object or a translucent object for all objects to be displayed. The operability is thereby remarkably improved.

Figure 8:
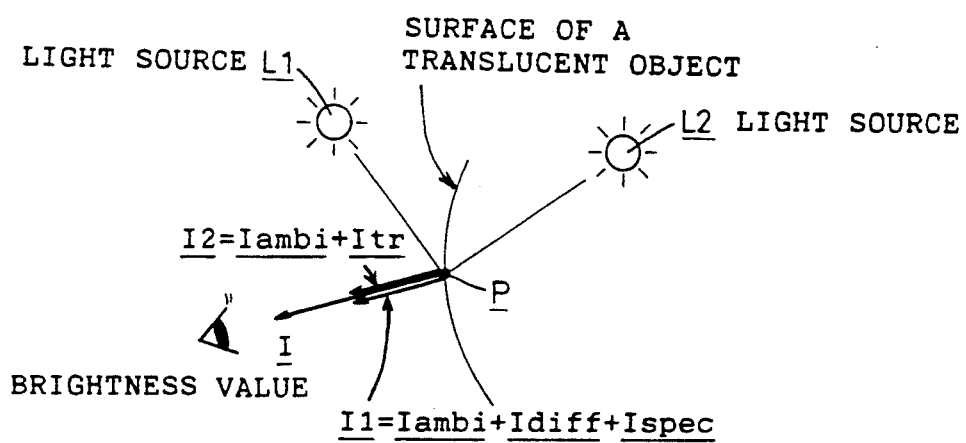
FIG. 8 is a schematic illustrative view showing two light sources.

FIG. 8 schematically illustrates a light source L1 on the same side as the viewpoint with respect to the object surface to be displayed, while another light source L2 is present on the side opposite the viewpoint side.

The brightness value I of a point P on the object surface to be displayed is obtained using the equation, $$I = (Iambi + Idiff + Itr + Ispec).$$

The brightness value I is a function of a brightness value I1 and a brightness value I2. The brightness value I1 is attribured to the light source L1 and is obtained by the following equation, $$I1 = Iambi + Idiff + Ispec.$$

The brightness value I2 is attributed to the light source L2 and is obtained by the following equation, $$I2 = Iambi + Itr.$$

As is apparent from the foregoing, display of an opaque surface is performed corresponding to the light source L1, while display of a translucent surface is performed corresponding to the light source L2. Display with superior realism is accordingly obtained.

Figure 9:
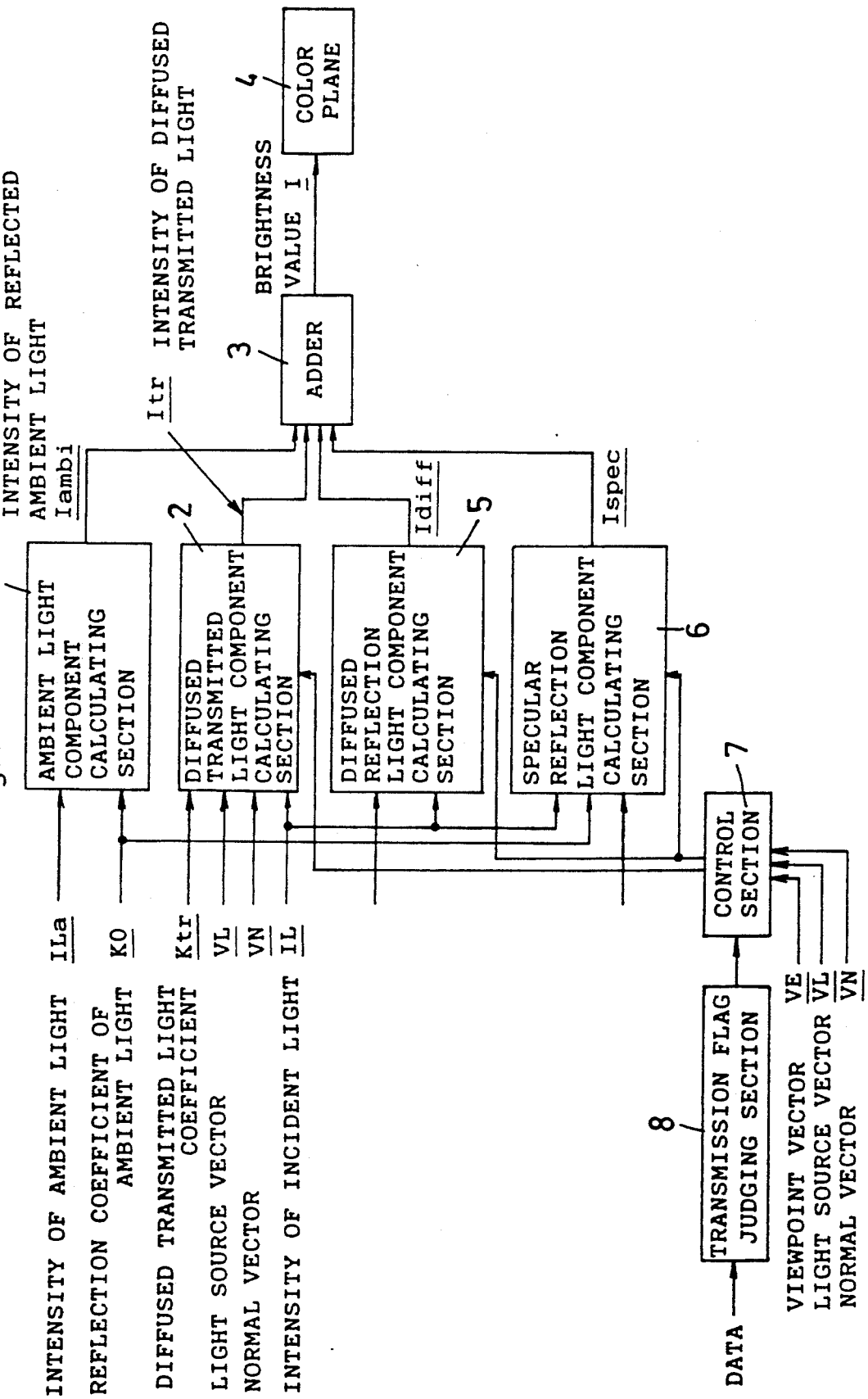
FIG. 9 is a block diagram of yet another embodiment of the apparatus for displaying a translucent object in accordance with the present invention.
Figure 10:
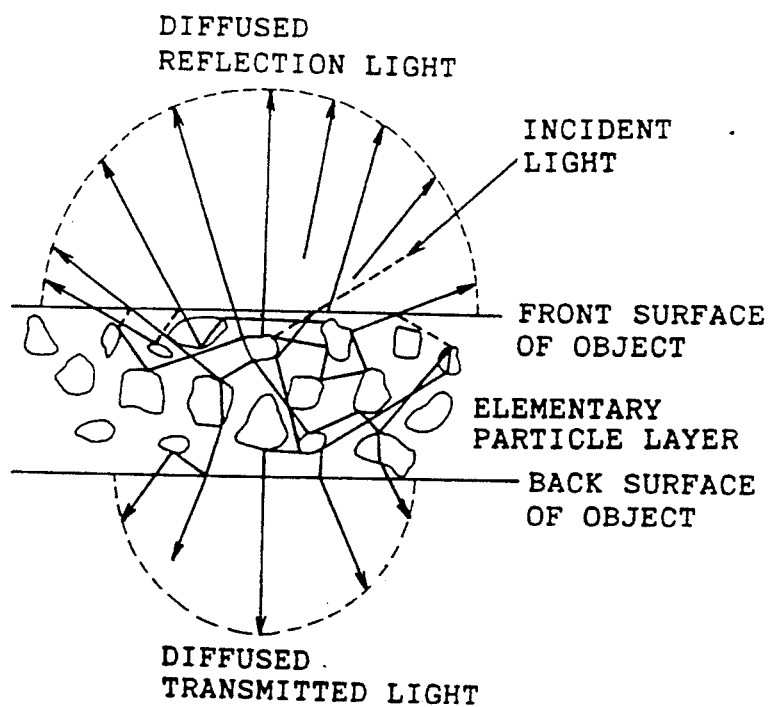
FIG. 10 is a schematic diagram useful in understanding diffused transmitted light.

FIG. 9 is a block diagram of still another embodiment of the apparatus for displaying translucent objects in accordance with the present invention.

The embodiment of FIG. 9 differs from the embodiment of FIG. 7 in that a transmission flag judging section 8 is further provided to control the operation of the control section 7. Also, a host processor (not shown) or the like provides a transmission flag f which indicates whether or not data displaying an object as a translucent object should be provided as additional data to surface data representative of a surface of the object. The trasmission flag judging section 8 judges whether or not the transmission flag f has been set. When the transmission flag f has been set, the transmission flag judging section 8 operates the control section 7 as described in connection with the embodiment of FIG. 7. On the contrary, when the transmission flag f has not been set, the transmission flag judging section 8 operates the control section 7 to perform an opaque object display operation.

In this embodiment, when objects which may be displayed as translucent objects and objects which are not to be displayed as translucent objects are present, the selection of whether to display an object as opaque or translucent is performed automatically.

In each embodiment, it is possible that the thickness of an object to be displayed can be visually represented by taking the transmissivity corresponding to the thickness of the object into consideration. It is also possible that the diffused transmitted light coefficient Ktr is a function of the intensity IL of the incident light so as to improve accuracy in the display of an object.

Various modifications and variations will occur to those skilled in the art without departing from the spirit and scope of the invention as defined by the appended claims.

What is claimed is:

1. A method for displaying a surface which forms a portion of an object to appear as an opaque surface or a translucent surface on a display screen defining a plurality of pixels, said method comprising the steps of:
   (1) producing viewpoint vector data representing a viewing direction from a viewpoint, light source vector data representing the direction of light from a light source, and normal vector data representing a vector which is normal to a portion of said surface which is to be displayed by plural pixels;
   (2) judging whether said viewpoint and said light source are in a first condition wherein said viewpoint and said light source are on a same side of said portion of said object, or whether said viewpoint and said light source are in a second condition wherein said viewpoint and said light source are on opposite sides of said portion based upon a relationship between said viewing direction and said direction of light from said light source with respect to said surface, said relationship being determined based upon said viewpoint vector data, said light source vector data and said normal vector data corresponding to one of said plural pixels;
   (3) if a judgement is made that said light source and said viewpoint are in said second condition, then said surface is displayed as a translucent surface by,
      (3a) providing a first intensity value corresponding to ambient light intensity,
      (3b) providing a second intensity value corresponding to diffused transmitted light intensity, said diffused transmitted light intensity being determined based upon the angle of incidence of incident light from said light source, said angle of incidence being determined based on said normal vector data and said light source vector data,
      (3c) providing a first brightness value based upon a combined intensity value obtained by combining said first and second intensity values, and (3d) storing said first brightness value in a frame memory and projecting said first brightness value stored in said frame memory on a corresponding pixel of said display screen whereby said screen is caused to visually display said surface as a translucent surface; and (4) if judgement is made that said light source and said viewpoint are in said first condition, then said surface is displayed as an opaque surface by, (4a) providing a first intensity value corresponding to ambient light intensity, (4b) providing a third intensity value corresponding to reflected light intensity, (4c) providing a second brightness value based upon a combined intensity value obtained by combining said first and third intensity values, and (4d) storing said second brightness value in a frame memory and projecting said second brightness value stored in said frame memory on a corresponding pixel of said display screen whereby said screen is to visually display said surface as an opaque surface.

2. A method for displaying a surface which forms a portion of an object to appear as an opaque surface or a translucent surface on a display screen as set forth in claim 1, wherein said second intensity is calculated based upon a coefficient, translucent object thickness, intensity of incident light from said light source, and said angle of incidence.

3. A method for displaying surfaces constituting an object to appear as an opaque surface or a translucent surface on a display screen as set forth in claim 1, wherein said step (3b) of providing a diffused transmitted light intensity comprises the steps of obtaining said diffused transmitted light intensity according to the relation:

$$Itr = Ktr \times IL \times \cos \theta;$$

where

Ktr is a coefficient which is a function of characteristics of material forming said translucent object;

IL is incident light intensity; and $\cos \theta$ is the product of the light source vector and the normal vector.

4. A graphics display apparatus for displaying a surface which forms a portion of an object to appear as an opaque surface or a translucent surface on a display screen defining a plurality of pixels, said apparatus comprising:

a frame memory having a memory region corresponding to each pixel defined for said display screen;

means for producing viewpoint vector data representing a viewing direction from a viewpoint, light source vector data representing the direction of light from a light source, and normal vector data representing a vector which is normal to a portion of said surface which is to be displayed by plural pixels;

an ambient light intensity obtaining means for obtaining an ambient light intensity corresponding to each pixel;

a reflected light intensity obtaining means for obtaining a reflected light intensity corresponding to each pixel;

a diffused transmitted light intensity obtaining means for obtaining diffused transmitted light intensity which is determined based upon the angle of incidence of incident light from said light source, said angle of incidence being determined based on said normal vector data and said light source vector data corresponding to each pixel;

judging means for judging whether or not said viewpoint and said light source are present on a same side of said portion of said object depending upon a relationship of said viewing direction and said direction of light from said light source with respect to said surface, and providing a control signal in response to a judgement made thereby, said relationship being determined based upon said viewpoint vector data, said light source vector data and said normal vector data corresponding to one of said plural pixels, said control signal causing said diffused transmitted light intensity obtaining means to be operative to obtain a diffused transmitted light intensity and causing said reflected light intensity obtaining means to be inoperative when a judgement is made that said viewpoint and light source on an opposite sides of said portion, and for causing said diffused transmitted light intensity obtaining means to be inoperative and said reflected light intensity obtaining means to be operative to obtain a reflected light intensity when a judgement is made that said viewpoint and said light source are on the same side of said portion;

brightness value obtaining means, interconnected to said frame memory, which stores obtained brightness values therein, said brightness value obtaining means being responsive to a judgement by said judging means that said viewpoint and said light source are on opposite sides of said portion, for combining an ambient light intensity obtained by said ambient light intensity obtaining means and a diffused transmitted light intensity obtained by said diffused transmitted light intensity obtaining means to obtain brightness values corresponding to display of said surface as a translucent surface, or responsive to a judgement by said judging means that said viewpoint and said light source are on a same side of said portion, for combining an ambient light intensity obtained by said ambient light intensity obtaining means and a reflected light intensity obtained by said reflected light intensity obtaining means to obtain brightness values corresponding to display of said surface as an opaque surface; and display means for visually displaying said surface by projecting brightness values stored in said frame memory on said display screen.

5. An apparatus as set forth in claim 4, wherein said diffused transmitted light intensity obtaining means obtains said diffused transmitted light intensity based upon said light source vector data and said normal vector data, characteristics of a material forming said object, and the thickness of said object.

6. An apparatus as set forth in claim 4, wherein said diffused transmitted light intensity obtaining means obtains said diffused transmitted light intensity according to the relation:

$$Itr = Ktr \times IL \times \cos \theta;$$

where

Ktr is a coefficient which is a function of characteristics of material forming said translucent object;

IL is incident light intensity; and $\cos \theta$ is the product of the light source vector and the normal vector.

* * * * *